United States Patent [19]
Schupp et al.

[11] 4,376,166
[45] Mar. 8, 1983

[54] NOCARDIA STRAIN

[75] Inventors: Thomas Schupp, Möhlin; Peter Traxler, Allschwil; Jakob Nüesch, Arlesheim, all of Switzerland

[73] Assignee: Ciba-Geigy Corporation, Ardsley, N.Y.

[21] Appl. No.: 270,184

[22] Filed: Jun. 3, 1981

Related U.S. Application Data

[62] Division of Ser. No. 112,898, Jan. 17, 1980, Pat. No. 4,298,692.

[51] Int. Cl.³ .............................................. C12N 1/20
[52] U.S. Cl. .................................................. 435/253
[58] Field of Search .............................. 435/253, 872

[56] References Cited
PUBLICATIONS

Schupp et al. J. Bacteriology vol. 121 No. 1 pp. 128–136.
Helvetia Chimica Acta vol. 56, Fasc. 7 (1973) No. 239-240-2279.

Primary Examiner—Alvin E. Tanenholtz
Attorney, Agent, or Firm—Michael W. Glynn; Norbert Gruenfeld; Prabodh I. Almaula

[57] ABSTRACT

New antibiotically active compounds having the basic structure of rifamycin S, namely 3-hydroxyrifamycin S (formula A: $X= > C=O$; $R^1=OH$; $R^2=H$), 3,31-dihydroxyrifamycin S (formula A: $X= > C=O$; $R^1=R^2=OH$) and 1-desoxy-1-oxarifamycin S (formula A: $X=-O-$; $R^1=R^2=H$)

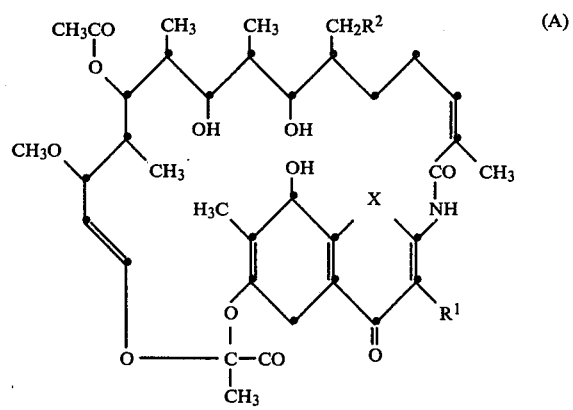

are formed by cultivating, under aerobic conditions, a strain of *Nocardia mediterranei* which is derived from *Streptomyces mediterranei* ATCC 13 685 as the parent strain and is characterized by the ability to produce at least one of the mentioned compounds. The recombinant strain *Nocardia mediterranei* DSM 1415 has proved suitable. The mentioned rifamycin S analogues have analogous antibiotic properties to this but have a wider range of action, especially against gram-negative bacteria.

1 Claim, No Drawings

NOCARDIA STRAIN

This is a division of application Ser. No. 112,898 filed on Jan. 17, 1980 now U.S. Pat. No. 4,298,692.

The subject of the invention is a group of new antibiotically active compounds having the basic rifamycin structure and consisting of 3-hydroxyrifamycin S of the formula I, 3,31-dihydroxyrifamycin S of the formula II and 1-desoxy-1-oxarifamycin S of the formula III

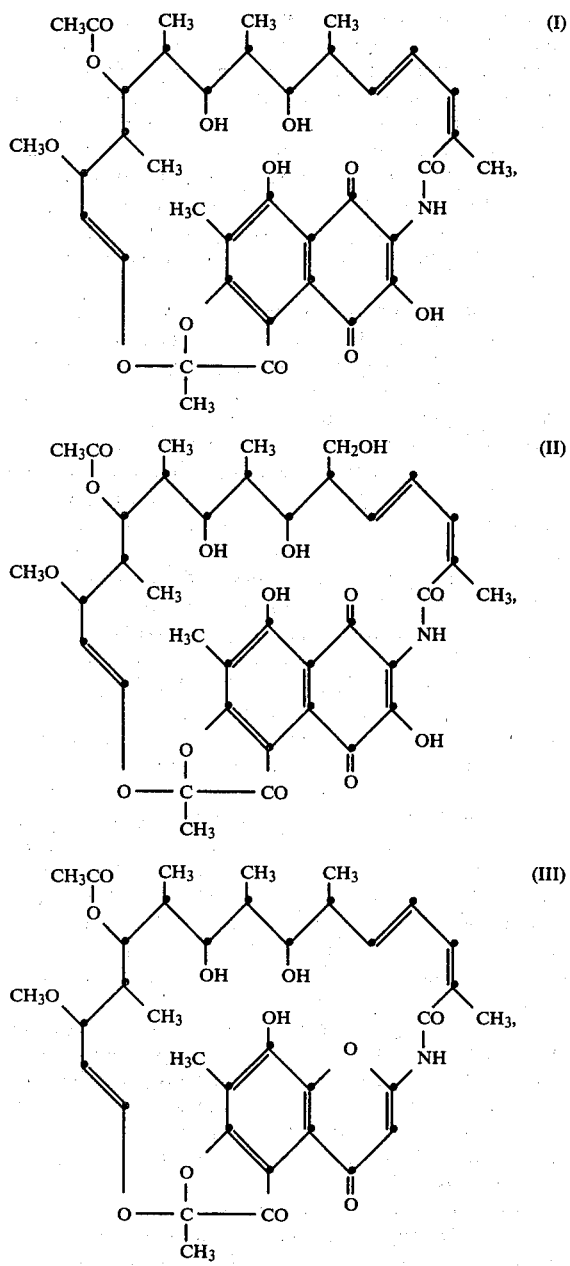

and a process for the preparation of the same by fermentative means, and also pharmaceutical preparations containing at least one of these compounds as active substance. The subject of the invention also includes the use of these compounds as antibiotics and for the manufacture of pharmaceutical preparations and also the medicinal methods for the treatment of infections in warm-blooded animals, especially human beings and domesticated animals, using each one of these compounds, especially in the form of a pharmaceutical preparation.

The compounds I–III according to the invention are distinguished by the following properties:

3-hydroxyrifamycin S (I) is an amorphous red powder, is readily soluble in most organic solvents, and is insoluble in water and aliphatic hydrocarbons.

The thin-layer chromatographic behaviour in comparison with rifamycin S is shown in Table 1:

TABLE 1

Rf values of compounds I–III and rifamycin S (thin-layer chromatography on silica gel plates 60 F 254, manufacturer: Merck, Darmstadt, Federal Republic of Germany).

|  | System 1 | System 2 | System 3 | System 4 |
|---|---|---|---|---|
| Rifamycin S | 0.65 | 0.74 | 0.62 | 0.42 |
| I | 0.10 | 0.37 | 0.18 | 0.61 |
| II | 0.04 | 0.16 | 0.03 | 0.36 |
| III | 0.30 | 0.40 | 0.19 | 0.43 |

System 1: chloroform/methanol (9:1)
System 2: chloroform/methanol (6:1)
System 3: ethyl acetate/acetone/water (72:24:4)
System 4: toluene/acetone/methanol (5:3:2)

In the field desorption mass spectrum, 3-hydroxyrifamycin S (I) has a sharp maximum of the molecular ion at m/e=711, which is consistent with the empirical formula $C_{37}H_{45}NO_{13}$, and thus differs only by 16 units of mass, corresponding to an oxygen atom, from the empirical formula of rifamycin S ($C_{37}H_{45}NO_{12}$).

In the infra-red spectrum (in $CH_2Cl_2$) of 3-hydroxyrifamycin S, the following bands, typical of rifamycins, are presents: 3450 (OH), 3350 (amide NH), 2950, 1740 (5-ring ketone), 1715 (acetate), 1685 (amide I), 1640 and 1615 (quinone C=O), 1510 (amide II), 1415, 1380, 1325, 1295, 1155, 1065 cm$^{-1}$.

The 360 MHz-NMR spectrum of the compound (see FIG. 1) is largely identical to that of rifamycin S except for the signal at 7.3 ppm which, in the case of rifamycin S, was attributed to the H(3) proton and is missing in the case of the compound according to the invention. In keeping with this, also in the $^{13}$C-NMR spectrum of the compound according to the invention the signal of the C(3) atom is found only at 162 ppm, that is to say, displaced substantially towards a lower field compared with rifamycin S, which indicates the presence of a hydroxyl group in this position (position 3). All these physical data clearly agree with the structural formula given above. For structure determination, nomenclature and numbering of the rifamycins, see V. Prelog and W. Oppolzer: Helv. Chim. Acta 56, 2279 (1973).

3,31-Dihydroxyrifamycin S (II) is an amorphous red powder, is readily soluble in most organic solvents and is insoluble in water and aliphatic hydrocarbons.

The behaviour in thin-layer chromatography in comparison with rifamycin S is shown in Table 1:

In the field desorption mass spectrum, 3,31-dihydroxyrifamycin S (II) has a molecular ion at m/e=727 which is consistent with the empirical formula $C_{37}H_{45}NO_{14}$ and thus differs only by 16 units of mass, corresponding to an oxygen atom, from the empirical formula of 3-hydroxyrifamycin S (I) ($C_{37}H_{45}NO_{13}$).

The infra-red spectrum (in $CH_2Cl_2$) is practically identical to that of 3-hydroxyrifamycin S. In the 360 MHz-NMR spectrum of the compound II, in comparison to that of rifamycin S, the signal, which, in the case of rifamycin S, was attributed to the H(3) proton, is again missing at 7.3 ppm. In addition, one of the signals of the secondary methyl groups in the ansa ring is also missing. However, an AB system reappears at 3.5 ppm and may be attributed to the primary hydroxy group at C(31). By means of double resonance tests, it is possible to show the coupling of the H(20) proton at 2.5 ppm with the vinyl proton H(19) at 5.95 ppm, with the H(21) proton at 4 ppm and also with the two H(31) protons.

In the $^{13}$C-NMR spectrum (see Table 2) C(31) is found at 62.3 ppm. However, only 7 signals are present for methyl groups between 8 and 22 ppm, compared with 8 such signals in rifamycin S and 3-hydroxyrifamycin S (I).

All these physical data are consistent with the postulated structural formula.

1-Desoxy-1-oxarifamycin S (III) is a light yellow amorphous powder, is readily soluble in most organic solvents, is insoluble in water and aliphatic hydrocarbons. The thin-layer chromatographic behaviour is shown in Table 1. 1-Desoxy-1-oxarifamycin S (III) differs from rifamycin G [G. Lancini et al.; Journal of Antib. 29 (4), 466 (1976)] only in the presence of the double bond C(16)-C(17).

In the mass spectrum, the compound III has a molecular ion at m/e 683 (rifamycin G has M+ at m/e 685), which is consistent with the empirical formula of $C_{36}H_{45}NO_{12}$. The IR spectrum is practically identical to that of rifamycin G.

In the 100 MHz-NMR spectrum (CDCl$_3$) the signals of the C(16)-C(17), C(17)-C(18) and C(28)-C(29) double bonds are present. As in the case of rifamycin G, the C(3) proton appears at 7.2 ppm.

The $^{13}$C-NMR spectrum also (in CD$_3$OD) is consistent with the postulated structure (see Table 2). The C(1) atom signal, which normally appears at 185 ppm in the case of rifamycins, is missing. The signals of the aromatic carbon atoms C(2), C(3) and C(9) also undergo drastic changes compared with rifamycin S.

The rifamycin analogues I-III according to the invention exhibit a very good antibiotic activity similar to that of rifamycin S, especially an antimicrobial activity, above all against gram-positive and gram-negative bacteria. They prove to be superior to rifamycin S in particular in their antibiotic activity against gram-negative bacteria, such as *Escherichia coli* and Pseudomonas sp.

According to the invention, the compounds I-III are obtained by isolation from fermentation material, in which they are formed, individually or together in any combination, by cultivating of certain strains of *Nocardia mediterrranei* described in more detail below.

The isolation is carried out physico-chemically by means of methods of separation known per se, especially by centrifugation, filtration, solvent extraction precipitation, crystallisation and chromatography, especially adsorption chromatography and partition chromatography. In a typical isolation process, the fermentation material (culture broth) is freed of mycelium by filtration, optionally using filter auxiliaries, such as diatomaceous earth, and the culture filtrate is subjected to extraction with an organic solvent which is water-miscible only to a limited extent, especially with ethyl acetate or a halogenated aliphatic hydrocarbon, such as methylene chloride, chloroform or trichloroethylene, in a discontinuous or continuous process, such as a countercurrent process. Before extraction, the culture filtrate is preferably adjusted to a pH of approximately 2-3 by adding an acid, for example a mineral acid, such as, especially, hydrochloric acid, sulphuric acid or phosphoric acid, or alternatively a strong organic acid, such as oxalic acid or citric acid. Volatile fractions, especially solvents, are removed from the organic solution by evaporation and the residue remaining (crude extract) is subjected to further processing.

In order to isolate the compounds I-III according to the invention and to remove the accompanying substances, for example other metabolites, especially other compounds having a basic rifamycin structure, and optionally also in order to separate individual compounds I-III from one another, the crude extract is further purified especially by chromatography, for example column chromatography. Silica gel, for example, is especially suitable as an adsorbent and a suitable solvent is, for example, chloroform to which 1-20% methanol is admixed in a gradually increasing proportion, 3-hydroxyrifamycin S normally being eluted at a methanol concentration of 1-5% and first 1-desoxy-1-oxarifamycin S and then 3,31-dihydroxyrifamycin S as well normally being eluted at a methanol concentration of 5-10%.

The purification process can be repeated if necessary, optionally using other adsorbents and/or solvent systems. The effectiveness of the purification can be tested in the normal manner by thin-layer chromatography, the above-mentioned conditions being especially advantageous for this. It is also possible to apply biological test methods or combine them with thin-layer chromatography, for example it is possible to test the antibiotic action of the individual fractions against a suitable, preferably specifically sensitive, micro-organism. A particularly suitable test organism is *Escherichia coli* and the combination of separation by thin-layer chromatography and bio-autographical detection has proved to be an especially good test method. In this case the developed chromatographic plate is pressed onto a germinating plate inoculated with a test organism, for example *Escherichia coli*, and the active substance is located by the formation of a corresponding inhibition zone.

In order to manufacture small quantities of 3-hydroxyrifamycin S in pure form, it is advantageous to use preparative thin-layer chromatography; suitable eluants for this purpose are, for example, silica gel thin-layer plates (like the above-mentioned plates F 254) and a mixture of chloroform and methanol (4:1 or 6:1), or of ethyl acetate, acetone and water (72:24:4) or of toluene, acetone and methanol (5:3:2). 3,31-Dihydroxyrifamycin S and 1-desoxy-1-oxarifamycin S are obtained in pure form in an analogous manner using the same plates and elution systems. The desired zone is separated off mechanically, collected and extracted with a suitable solvent, preferably ethyl acetate, in order to isolate the pure product. If necessary, this purification process can be repeated using various adsorbents and/or solvent combinations.

Fermentation material which contains 3-hydroxyrifamycin S, 3,31-dihydroxyrifamycin S and/or 1-desoxy-1-oxarifamycin S and which is used to isolate these compounds in the manner described above, is obtained according to the invention by cultivating, under aerobic conditions in a liquid medium, a strain of *Nocardia mediterranei* that is derived from *Streptomyces mediterranei* ATCC 13685 as the parent strain and is characterised by its ability to produce at least one of the compounds according to the invention of the group consisting of 3-hydroxyrifamycin S, 3,31-dihydroxyrifamycin S and 1-desoxy-1-oxarifamycin S. Of these strains, recombinant strains which are resistant to streptomycin and autotrophic with respect to amino acids are preferred.

The liquid nutrient medium used is, for example, an aqueous solution or suspension that contains at least one carbon source (which also serves as a source of energy) and at least one nitrogen source, and preferably also mineral substances. Examples of carbon sources are: glycerin, carbohydrates that can be assimilated, such as sugcyclitols, for example mannitol, polysaccharides, for example starch, disaccharides, for example lactose and saccharose, and monosaccharides, especially glucose, and also suitable carbohydrate-containing industrial raw materials, such as sugar beet molasses and sugar cane molasses. Examples of nitrogen sources are: amino acids, especially the naturally occurring α-amino acids, peptides and also proteins and the decomposition products thereof, such as peptones and tryptones, and also ammonium salts and nitrates, as well as suitable industrial nitrogen-containing raw materials, such as meat extracts, casein hydrolysate and yeast autolysate and yeast extract. Mixed industrial carbon and nitrogen sources, such as various plant seeds, are also suitable and are used in the form of aqueous extracts, meal or pulps of beans, for example soya beans, and cereal grains, for example wheat and especially maize ("corn-steep liquor"); also cotton seeds, and malt extract. Apart from ammonium salts and nitrates, the nutrient medium may contain as inorganic salts chlorides, carbonates, sulphates and especially phosphates of alkali metals and alkaline earth metals, and also of trace elements, such as magnesium, iron, zinc and manganese.

In the conventional manner, the nutrient medium is prepared, sterilised and inoculated with a culture of the production strain while observing the normal precautions. The cultivation is carried out under aerobic conditions, for example in a stationary surface culture or preferably in a submerged culture that is supplied with oxygen, normally in the form of atmospheric oxygen, by shaking and/or stirring, for example in shaking flasks or fermenters of known construction. A suitable temperature is between approximately 20° and approximately 35° C., preferably approximately 22°–30° and especially 28° C. The culture is carried out at a pH of approximately 5.0–9.0, preferably in the range of from approximately 6.0–8.0 and especially in the region of the neutral point. Normally, further adjustment of the pH is unnecessary during fermentation. Under these conditions, the maximum quantity of 3-hydroxyrifamycin S is produced in the course of approximately 3 to 14, normally 7, days and is secreted into the nutrient medium. In the case of relatively large batches, growth is effected stepwise, one or more pre-cultures first being allowed to grow in a liquid nutrient medium for a relatively short period, for example approximately 2-3 days and transferred by inoculation into a large quantity of nutrient medium, for example twenty times the quantity, until the desired production volume is reached.

The production micro-organism according to the invention, that is to say, a strain of *Nocardia mediterranei* producing at least one of the compounds of the group consisting of 3-hydroxyrifamycin S, 3,31-dihydroxyrifamycin S and 1-desoxy-1-oxarifamycin S, may be obtained by growing a mutant or recombinant strain of *Nocardia mediterranei* which is intended for testing and is derived from *Streptomyces mediterranei* ATCC 13 685 as the parent strain, and testing the resulting fermentation material for the presence of 3-hydroxyrifamycin S, 3,31-dihydroxyrifamycin S and/or 1-desoxy-1-oxarifamycin S, for example as described below. An advantageous recombinant strain is obtained for example, by crossing of and selective gene exchange between two *Nocardia mediterranei* mutants A and B which are derived from *Streptomyces mediterranei* ATCC 13 685 as the parent strain, [compare T. Schupp et al.: Journal of Bacteriology 121, 128–136 (1975)]. (The parent strain was deposited under the original taxonomic name *Streptomyces mediterranei* (Margalith and Bretta) in the ATCC collection under number 13 685. Later, as a result of further examination, this name was revised and the name *Nocardia mediterranei* (Thieman et al.) ATCC 13 685 was proposed. Here, the original collection name is used.)

The mutant strains A and B are in their turn obtained in a manner known per se by the mutagenic action of ultraviolet light or N-methyl-N'-nitro-N-nitrosoguanidine on the mycelium suspension of the parent strain *Streptomyces mediterranei* ATCC 13 685 and are isolated by selection in accordance with their specific properties. The mutant strain A produces chiefly rifamycin B, and is in this respect similar to the parent strain, but compared therewith has, on the one hand, a resistance towards streptomycin that is 50 times as great, but, on the other hand, is auxotrophic with respect to cysteine, lysine and leucine, that is to say, it needs these three amino acids to grow. The mutant strain B is distinguished especially because it is sensitive to streptomycin, and particularly because it does not produce rifamycin B, but only an intermediate of rifamycin synthesis, rifamycin W [compare R. J. White et al.: Proc. Nat. Acad. Sc. USA 71, 3260–3269 (1974)]. The recombination is carried out in a manner known per se, by cultivating both mutant strains together, and isolating the recombinant strain in accordance with its specific properties by selection in accordance with known methods; for the methods, compare, for example, the above-mentioned publication of T. Schupp et al.

An especially important operation for the isolation of the desired recombinant strain is the joint incubation of both mutants A and B on a complete medium, for example, culture medium No. 2, and subsequently cultivating the resulting mixed culture on a selective minimal medium, for example the culture medium No. 3 described hereinafter. It is especially characteristic of such a minimal medium that, in addition to a carbon and energy source that is as simple as possible, such as a simple sugar, for example glucose, it contains only inorganic salts, especially an inorganic ammonium salt, as the sole source of nitrogen. On such a selective minimal medium neither the auxotrophic A strain is able to grow, because the amino acids leucine, cysteine and lysine it needs are not present, nor is the B strain able to grow, because it is inhibited by 0.025 g/l of streptomycin. Thus, after incubation, only colonies of recombinant strains are found on the medium used, to which, by gene exchange, the increased resistance to streptomycin has been transferred from strain A as well as, from strain B, the ability to grow without the amino acids leucine, cysteine and lysine. From several recombinant strains selected in this manner the desired culture producing the rifamycin analogues according to the invention is obtained by separate cultivating of individual colonies and by assaying for the presence of 3-hydroxyrifamycin S, 3,31-dihydroxyrifamycin S and/or 1-desoxy-1-oxarifamycin S amongst the metabolites. This assay is effected chiefly by extracting the culture filtrate with an organic solvent, as described above, and by the combined thin-layer chromatographic separation and bioautographic detection of the desired antibiotic, especially using *Escherichia coli* as the test micro-organism.

An especially suitable, typical mutant strain A is the mutant strain *Nocardia mediterranei* T 104, and an especially suitable mutant strain B is the mutant strain *Nocardia mediterranei* T 191 (both derived from the strain *Streptomyces mediterranei* ATCC 13 685 as the parent strain). These specific mutant strains have the properties characteristic of the mutant strains A and B in their entirety. By recombination of the strains T 104 and T 191 mentioned, and by selective isolation, as described above, in particular the recombinant strain *Nocardia mediterranei* R 21 is obtained, which was deposited under the name *Nocardia mediterranei* DMS 1 415 in the German Collection of Micro-organisms, Göttingen, Federal Republic of Germany on Dec. 29, 1978. The respective Nocardia strains are registered in the microorganism collection of Ciba-Geigy AG., 4002 Basle, Switzerland, under T 104, T 191 and R 21). The recombinant strain R 21 has the above-specified characteristic properties of a preferred recombinant strain producing 3-hydroxyrifamycin S according to the invention, because it produces this compound as the main product, and then 3,31-dihydroxyrifamycin S and 1-desoxy-1-oxarifamycin S as essential accompanying substances, is autotrophic with respect to amino acids, and, compared with the parent strain ATCC 13 685, is 50 times more resistant to streptomycin. In its other features, especially in its morphology, no characteristic differences from the parent strain ATCC 13 685 can be established.

The invention also includes the use of 3-hydroxyrifamycin S, 3,31-dihydroxyrifamycin S and 1-desoxy-1-oxarifamycin S, alone or in combination with one another or with other antibiotics, especially those antibiotics of the rifamycin type, as an antibiotic for combating infections that are caused by bacteria, for example those mentioned, both in the form of a drug and also of a disinfectant. When used as a drug, the active substance mentioned is administered to warm-blooded animals, especially to human beings, preferably in the form of a pharmaceutical preparation together with at least one conventional pharmaceutical carrier or auxiliary.

For the purpose of producing pharmaceutical preparations, each one of the mentioned compounds according to the invention, especially 3-hydroxyrifamycin S, can be blended with an inorganic or organic carrier material suitable for topical, enteral or parenteral administration. Suitable substances for carrier materials are those that do not react with the new compound, such as, for example, gelatin, lactose, starch, magnesium stearate, vegetable oils, benzyl alcohol or other medicinal carriers. The pharmaceutical preparations may exist as, for example, tablets, dragees, powders, suppositories, or in liquid form, as solutions, suspensions, emulsions, creams or salves. They are optionally sterilised and/or contain auxiliaries such as preservatives, stabilisers, wetting agents or emulsifiers. They may also contain other therapeutically valuable substances. The disinfectants also may be mixed with suitable carriers, as is known.

The dosage of the active substances (3-hydroxyrifamycin S, 3,31-dihydroxyrifamycin S and 1-desoxy-1-oxarifamycin S, is effected in principle analogously to that of recognised antibiotics of the rifamycin type, and especially the dosage of rifamycin S; however, it is dependent also, firstly, on the species, body weight, age and individual condition of the warm-blooded animal, and, secondly, on the method of administration and especially on the particular sensitivity of the causative organism.

The invention also relates to a method for killing or inhibiting the growth of a micro-organism sensitive to at least one of the compounds I–III according to the invention, such as 3-hydroxyrifamycin S, the method being characterised by treating this micro-organism or a medium infected by this micro-organism with an antimicrobially active dose of one of the compounds I–III of the invention, especially 3-hydroxyrifamycin S. The term "an antimicrobially active dose" means an amount of the active substance that is sufficient for an effective inhibition of the particular micro-organism to be treated.

The following Examples illustrate the above-described invention, but shall in no way limit it in its scope. Temperatures are given in degrees Centigrade. The composition of the mixtures of solvents is given in volume ratio.

The following nutrient media are used:

| Culture medium No. 1 | |
| --- | --- |
| glucose | 22 g |
| beef extract | 5 g |
| peptone | 5 g |
| brewer's yeast extract | 5 g |
| enzymatic casein hydrolysate | 3 g |
| NaCl | 1.5 g | made up with distilled water to 1000 ml, pH set at 7.0, sterilisation carried out for 20 minutes at 120° C.

| Culture medium No. 2 | |
| --- | --- |
| brewer's yeast extract | 4 g |
| malt extract | 10 g |
| glucose | 4 g |
| agar | 20 g | made up with distilled water to 1000 ml, pH adjusted to 7.3 with KOH before sterilisation, sterilisation carried out for 20 minutes at 120° C.

| Culture medium No. 3 | |
| --- | --- |
| $K_2HPO_4$ | 1.0 g |
| $(NH_4)_2SO_4$ | 2.0 g |
| $MgSO_4.7H_2O$ | 1.0 g |
| NaCl | 1.0 g |
| $CaCO_3$ | 1.0 g |
| $FeSO_4.7H_2O$ | 0.001 g |
| $MnCl_2.4H_2O$ | 0.001 g |
| $ZnSO_4.7H_2O$ | 0.001 g |
| agar | 20.0 g | made up with distilled water to 1000 ml. Sterilisation carried out for 20 minutes at 120° C.

Under sterile conditions, there are added to the resulting, still hot solution:

(a) 20 ml of a glucose solution, prepared by dissolving 50 g of glucose in distilled water, making up to 100 ml and sterilising for 20 minutes at 120° C., and (b) 5 ml of a streptomycin solution prepared by dissolving 0.5 of streptomycin in 100 ml of distilled water and sterile filtering.

| Culture medium No. 4 | |
|---|---|
| brewer's yeast extract | 3 g |
| peptone | 5 g |
| malt extract | 3 g |
| saccharose | 10 g |
| agar | 20 g | made up with distilled water to 1000 ml. Sterilisation carried out for 20 minutes at 120° C.

EXAMPLE 1

(Isolation of the recombinant strain R 21)

The two mutant strains T 104 and T 191 of *Nocardia mediterranei* to be crossed are incubated separately in 40 ml each of the culture medium No. 1 for 3 days on a rotary shaker at 250 rev/min and 28° C. 2 ml of the culture solution of each strain are then introduced into a sterile test tube and mixed vigorously. An agar slant (=culture medium No. 2) is inoculated with 0.2 ml of this mixture.

The agar slant culture is incubated for 6 days at 28° C. (In this phase, the exchange of genes between the two strains T 104 and T 191 takes place). After incubation, sufficient distilled water is added under sterile conditions to the agar slant culture for the mycelium adhering to the surface of the agar to be brought into suspension by scratching with a loop. This suspension is introduced into a sterile test tube and shaken vigorously with sterile quartz beads of 2-3 mm diameter for 2 minutes. The resulting suspension of short pieces of mycelium is then washed by twice centrifuging and resuspending in distilled water, and diluting 100-fold with distilled water. 0.1 ml in each case of this diluted suspension is plated onto Petri dishes containing a selective minimal medium (=culture medium No. 3). The inoculated Petri dishes are incubated for 10-14 days at 28° C., as a result of which only the autotrophic recombinant resistant to streptomycin can grow and the original mutants remain inhibited. To isolate recombinant strains producing 3-hydroxyrifamycin S, from each colony grown an agar slant of the culture medium No. 4 is inoculated and incubated for 8 days at 28° C. Of these cultures, one loopful of mycelium each is inoculated into 20 ml of the culture solution No. 1 in small Erlenmeyer flasks, and these are kept at 28° C. on a rotary shaker at 250 rev/min. After 7 days' incubation, the culture solutions are filtered through paper filters, the resulting culture filtrate is acidified to pH 2.5 with hydrochloric acid and extracted with the same volume of methylene chloride. The resulting extract is concentrated by evaporation to 1/20 of the quantity, and developed by thin-layer chromatography on silica gel 60 F 254 plates (Merck) using the elution system chloroform/methanol (4:1). By pressing these developed thin-layer plates onto *Escherichia coli* germinating plates (bio-autogram), an inhibition zone (Rf 0.45) indicates which of the extracts under investigation contains 3-hydroxyrifamycin S, and thus which of the recombinant strains under investigation produces 3-hydroxyrifamycin S. The recombinant strain R 21 isolated in this manner was deposited in the German Collection of Micro-organisms, as stated above, under the name *Nocardia mediterranei* DSM 1415.

EXAMPLE 2

Fermentative preparation of 3-hydroxyrifamycin S (I) and/or compounds II and III.

The strain *Nocardia mediterranei* R 21 is cultivated on an agar slant culture (culture medium No. 4) for 7-8 days at 28° C. 5 Erlenmeyer flasks each containing 40 ml of culture medium No. 1 are inoculated with the mycelium of this culture. The flasks are kept for 72 hours at 28° C. and 250 rev/min on the rotary shaker. After 72 hours' growth, 150 ml of the vegetative culture are used to inoculate 3 liters of culture medium No. 1. The fermentation is carried out with, in each case, 40 ml of medium in 200 ml capacity Erlenmeyer flasks for 7 days on the rotary shaker at 250 rev/min and 28° C.

EXAMPLE 3

[Isolation and preparation in pure form of 3-hydroxyrifamycin S (I), 3,31-dihydroxyrifamycin S (II) and 1-desoxy-1-oxarifamycin S (III)].

The fermentation material obtained according to Example 2 (3 liters), is filtered through diatomaceous earth, the filtrate is adjusted to pH 2.5 with 1 N hydrochloric acid, and extracted three times with chloroform. The aqueous phase is discarded and the organic phase is concentrated in vacuo. The resulting dark-coloured crude extract (2.02 g) is dissolved in 200 ml of methanol, 10 g of silica gel is added, and the mixture is evaporated to dryness. The powdery residue is placed onto the top of a chromatographic column (diameter 1 cm, height 40 cm) of 100 g of silica gel (Merck, particle size 65-200 nm). The elution is carried out with solvent mixtures of chloroform and a gradually increasing concentration (1-20%) of methanol. Individual fractions (each 25 ml) are concentrated by evaporation in a water jet vacuum and dried in a high vacuum. The fractions are combined on the basis of thin-layer chromatography (and optionally also a bio-autographic assay); the main portion of 3-hydroxyrifamycin S (I) is located in the fractions containing 1-5% of methanol; 1-desoxy-1-oxarifamycin S (III) and 3,31-dihydroxyrifamycin S (II) are then found in those fractions containing 5-10% of methanol.

For further purification (for example for ranalytical purposes), crude products I, II and III are chromatographed on thin-layer plates (silica gel 60 F 254, see above) with mixtures of chloroform/methanol (4:1) or (6:1), ethyl acetate/acetone/water (72:24:4) or toluene/acetone/methanol (5:3:2). The desired zone is separated off mechanically and extracted with ethyl acetate. The extract is washed with a dilute citric acid solution, dried and concentrated by evaporation. Pure 3-hydroxyrifamycin S and 3,31-dihydroxyrifamycin S are obtained, each in the form of an amorphous red powder, and also 1-desoxy-1-oxarifamycin S as a light yellow powder. Each of the compounds is readily soluble in methanol, ethanol and other lower alkanols, acetone, dimethyl sulphoxide, ethyl acetate, dioxan, tetrahydrofuran, ether, dimethylformamide, chloroform, methylene chloride and other similar chlorinated lower aliphatic hydrocarbons, and almost insoluble in pentane, hexane and similar aliphatic hydrocarbons and in water. Their behaviour in thin-layer chromatography, especially in comparison with rifamycin S, is given in Table 1 above.

3-Hydroxyrifamycin S (I)

Physical data: field desorption mass spectrum: M+ at m/e 711 ($C_3H_{45}NO_{13}$): UV spectrum:
(a) in ethanol: $\lambda_{max}$ ($\epsilon$) 230 (29600), 260 sh, 305 sh, 335 sh, 602 (240);
(b) in 0.01-N HCl: $\lambda_{max}$ ($\epsilon$) 267 (14900), 305 sh, 342 (4600);
(c) in 0.01-N NaOH: $\lambda_{max}$ ($\epsilon$) 245 sh, 308 (24500), 440 (5200).

Infra-red spectrum (in $CH_2Cl_2$): bands at 3450, 3350, 2950, 1740, 1715, 1685, 1640, 1615, 1510, 1415, 1380, 1325, 1295, 1155 and 1065 cm$^{-1}$; 360 MHz-NMR spectrum (in $CDCl_3$): see FIG. 1.

$^{13}$C-NMR spectrum (in $CDCl_3$): see Table 2.

3,31-Dihydroxyrifamycin S (II)

Physical data: field desorption mass spectrum: M+ at m/e 727 ($C_{37}H_{45}NO_{14}$); infra-red spectrum (in $CH_2Cl_2$): bands at 3450, 3350, 2950, 1740, 1715, 1685, 1640, 1615, 1510, 1410, 1385, 1320, 1290, 1155 and 1065 cm$^{-1}$; 360 MHz-NMR spectrum (in $CDCl_3$) (only the most important signals):

| ppm | Assignment | ppm | Assignment |
|---|---|---|---|
| 0.1 | } { $CH_3$(32,33,34) | 3.95 | H(21) |
| 0.6 | | 4.6 | H(25) |
| 1.0 | | | |
| 1.7 | $CH_3$(13) | 5.0 | H(28) |
| 1.95 | $CO-CH_3$ | 5.95 | H(19) |
| 2.0 | $CH_3$(30) | 6.1 | H(29) |
| 2.25 | $CH_3$(14) | 6.3 | H(17) |
| 2.45 | H(20) | 6.45 | H(18) |
| 2.95 | H(23) | 8.4 | NH—CO |
| 3.05 | O—$CH_3$ | | |
| 3.3 | H(27) | 12.7 | —OH(8) |
| 3.5 | H(31) | | |

$^{13}$C-NMR spectrum (in $CDCl_3$): see Table 2.

1-Desoxy-1-oxarifamycin S (III)

Physical data: mass spectrum: M+ at m/e 683 ($C_{36}H_{45}NO_{12}$); IR spectrum (in $CH_2Cl_2$): bands at 3450, 2950, 1740 sh, 1710, 1650, 1595, 1520, 1245, 1155, 1060 cm$^{-1}$.

100 MHz-NMR spectrum ($CDCl_3$)

| ppm | Assignment | ppm | Assignment |
|---|---|---|---|
| 0.6–1.1 | 3-CH—$CH_3$ | 5.24 | H(28) |
| 1.72 | $CH_3$(13) | 5.72 | H(19) |

| ppm | Assignment | ppm | Assignment |
|---|---|---|---|
| 2.0 | { $CO-CH_3$ / $CH_3$(30) | 6.24 | H(29) |
| 2.26 | $CH_3$(14) | 6.32 | H(17) |
| 3.1 | O—$CH_3$ | 6.4 | H(18) |
| 4.7 | H(25) | 7.2 | H(3) |

$^{13}$C-NMR spectrum (in $CD_3OD$): see Table 2.

TABLE 2

$^{13}$C—NMR data of rifamycin S, 3-hydroxyrifamycin S (I), 3,31-dihydroxyrifamycin S (II) and 1-desoxy-1-oxarifamycin S (III).

| Assignment C—Atom | Rifamycin S (CDCl$_3$) | I (CDCl$_3$) | II (CDCl$_3$) | III (CD$_3$OD) |
|---|---|---|---|---|
| 1 | 184.5 | 184.5 | 185.0 | — |
| 2 | 139.4 | 118.4 | 118.3 | 171.6 |
| 3 | 117.4 | 146.8 | 147.1 | 99.2 |
| 4 | 181.6 | 177.2 | 177.3 | 178.8 |
| 5 | 111.2 | 111.0 | 111.0 | 109.1 |
| 6 | 166.5 | 171.9 | 172.0 | 155.9 |
| 7 | 115.7 | 116.8 | 116.7 | 115.4 |
| 8 | 172.2 | 166.4 | 166.5 | 156.8 |
| 9 | 111.0 | 109.8 | 109.7 | 143.5 |
| 10 | 131.3 | 129.1 | 129.1 | 120.0 |
| 11 | 191.1 | 191.8 | 192.0 | 194.1 |
| 12 | 108.6 | 108.1 | 107.9 | 106.4 |
| 13 | 22.2 | 22.0 | 21.8 | 22.2 |
| 14 | 7.4 | 7.6 | 7.7 | 8.5 |
| 15 | 169.0 | 171.4 | 171.2 | 169.8 |
| 16 | 131.0 | 128.8 | 129.5 | 131.4 |
| 17 | 133.2 | 135.3 | 135.0 | 134.7 |
| 18 | 124.4 | 123.9 | 127.0 | 125.3 |
| 19 | 142.2 | 143.0 | 138.2 | 142.6 |
| 20 | 39.2 | 38.3 | 46.5 | 40.2 |
| 21 | 73.6 | 73.2 | 69.2 | 74.0 |
| 22 | 33.0 | 32.8 | 32.9 | 34.0 |
| 23 | 77.7 | 77.4 | 77.5 | 77.7 |
| 24 | } 37.4 | { 37.6 | { 37.6 | { 38.9 |
| 26 | } 37.4 | { 37.4 | { 37.8 | { 38.4 |
| 25 | 73.6 | 73.5 | 73.6 | 74.0 |
| 27 | 81.9 | 81.3 | 80.5 | 82.7 |
| 28 | 115.7 | 115.6 | 116.5 | 118.3 |
| 29 | 145.3 | 144.7 | 144.0 | 146.1 |
| 30 | 20.0 | 20.1 | 20.1 | 20.2 |
| 31 | 16.8 | 16.9 | [62.3] | 17.3 |
| 32 | } 11.4 | { 11.3 | 11.1 | 11.4 |
| 34 | } 11.4 | { 11.6 | 11.8 | 12.4 |
| 33 | 8.8 | 8.9 | 8.7 | 9.4 |
| 35 | 172.6 | 173.0 | 173.0 | 172.9 |
| 36 | 20.9 | 21.0 | 20.9 | 21.1 |
| 37 | 56.8 | 56.8 | 56.9 | 56.5 |

We claim:
1. A biologically pure culture of the microorganism Nocardia mediterranei strain DMS 1415.

* * * * *